United States Patent
Statham

(10) Patent No.: US 10,054,557 B2
(45) Date of Patent: Aug. 21, 2018

(54) METHOD FOR MEASURING THE MASS THICKNESS OF A TARGET SAMPLE FOR ELECTRON MICROSCOPY

(71) Applicant: Oxford Instruments Nanotechnology Tools Limited, Oxon (GB)

(72) Inventor: Peter Statham, Buckinghamshire (GB)

(73) Assignee: OXFORD INSTRUMENTS NANOTECHNOLOGY TOOLS LIMITED (GB)

( * ) Notice: Subject to any disclaimer, the term of this patent is extended or adjusted under 35 U.S.C. 154(b) by 0 days.

(21) Appl. No.: 15/329,902

(22) PCT Filed: Jul. 29, 2015

(86) PCT No.: PCT/GB2015/052188
§ 371 (c)(1),
(2) Date: Jan. 27, 2017

(87) PCT Pub. No.: WO2016/016644
PCT Pub. Date: Feb. 4, 2016

(65) Prior Publication Data
US 2017/0269011 A1    Sep. 21, 2017

(30) Foreign Application Priority Data

Jul. 29, 2014 (GB) .................................. 1413422.5

(51) Int. Cl.
*H01J 37/26* (2006.01)
*G01N 23/2252* (2018.01)
(52) U.S. Cl.
CPC ........ *G01N 23/2252* (2013.01); *H01J 37/261* (2013.01); *G01N 2223/304* (2013.01);
(Continued)
(58) Field of Classification Search
CPC ..................... H01J 37/261; H01J 2237/24578
See application file for complete search history.

(56) References Cited

U.S. PATENT DOCUMENTS 5,068,539 A  *  11/1991  Nogami .............. H01J 37/3171
                                                          250/398
6,788,760 B1     9/2004  Janik et al.
(Continued)

FOREIGN PATENT DOCUMENTS

JP           64-16905 A      1/1989
JP        2002-333412 A     11/2002

OTHER PUBLICATIONS

M. Watanabe et al., "The Quantitative Analysis of Thin Specimens: A Review of Prgress from the Cliff-Lorimer to the new Zeta-Factor Methods", Journal of Microscopy, vol. 221, No. 2, Feb. 23, 2006, pp. 89-109.

(Continued)

*Primary Examiner* — Jason McCormack
*Assistant Examiner* — Sean Luck
(74) *Attorney, Agent, or Firm* — Blank Rome LLP

(57) ABSTRACT

A method is provided of measuring the mass thickness of a target sample for use in electron microscopy. Reference data are obtained which is representative of the X-rays (28) generated within a reference sample (12) when a particle beam (7) is caused to impinge upon a region (14) of the reference sample (12). The region (14) is of a predetermined thickness of less than 300 nm and has a predetermined composition. The particle beam (7) is caused to impinge upon a region (18) of the target sample (16). The resulting X-rays (29) generated within the target sample (16) are monitored (27) so as to produce monitored data. Output data are then calculated based upon the monitored data and the reference data, the output data including the mass thickness of the region (18) of the target sample (16).

17 Claims, 6 Drawing Sheets

(52) U.S. Cl.
CPC .......... *G01N 2223/633* (2013.01); *H01J 2237/24578* (2013.01)

(56) References Cited

U.S. PATENT DOCUMENTS

| | | | | |
|---|---|---|---|---|
| 9,343,275 | B1* | 5/2016 | Chen | H01J 49/0004 |
| 2003/0071222 | A1* | 4/2003 | Harvey | G01R 29/24 |
| | | | | 250/397 |
| 2007/0085033 | A1* | 4/2007 | Buller | B82Y 10/00 |
| | | | | 250/492.1 |

OTHER PUBLICATIONS

J. M. Dijkstra et al., "Quantitative EPMA and TEM of Unsupported Films", Mikrochimica Acta., vol. 114-115, No. 1, Dec. 1994, pp. 277-284.

M. Nacucchi et al., "Experimental Check of the Use of Unconventional Reference Materials for EDS Analysis in a TEM by Extrapolation Method Based on Pure Elements", IOP Conference Series: Materials Science and Engineering, vol. 32, Mar. 7, 2012, pp. 1-11.

G. Kothleitner et al., "Linking TEM Analytical Spectroscopies for an Assumptionless Compositional Analysis", Microscopy and Microanalysis, vol. 20, No. 3, Mar. 6, 2014, pp. 678-686.

C.L. Churms et al., "Instrument-Invariant Method of Film Thickness Determination by Means of Substrate-to-Film X-Ray Peak Intensity Ratioing", Thin Solid Films, vol. 148, 1987, pp. 67-74.

Jean-Louis Pouchou, "X-Ray Microanalysis of Stratified Specimens", Analytica Chimica Acta, vol. 283, 1993, pp. 81-97.

* cited by examiner

METHOD FOR MEASURING THE MASS THICKNESS OF A TARGET SAMPLE FOR ELECTRON MICROSCOPY

RELATED APPLICATIONS

This application is a national phase of PCT/GB2015/052188, filed on Jul. 29, 2015, which claims the benefit of United Kingdom Application No. 1413422.5, filed on Jul. 29, 2014. The content of these applications are hereby incorporated by reference.

FIELD OF THE INVENTION

The present invention relates to a method of measuring the mass thickness of a target sample for use in electron microscopy, such as in transmission electron microscopy.

BACKGROUND TO THE INVENTION

Specimens for use in a transmission electron microscope (TEM) are prepared so that they are sufficiently thin to allow incident electrons to be transmitted through the specimen so that they can form a high resolution image. The TEM lens conditions can also be modified so that a diffraction pattern can be obtained. In order to achieve a condition wherein the specimen, which is typically less than 200 nm thick in the direction of the electron beam, is electron-transparent, the incident electrons are typically accelerated to energies between 80 keV and 400 keV.

Often such instruments can also be run in a scanning TEM mode (STEM), wherein a finely-focussed spot is deflected in a raster pattern over the specimen and a signal from transmitted or secondary electrons is recorded at each position so that the image is built up in a serial fashion. It is useful to know the thickness of a specimen because this can be used in the calculation of its other properties, such as point defect or dislocation density. Several techniques exist for measuring thickness in the TEM, which are based on measurement of transmitted or scattered electron signals or on analysis of electron diffraction patterns.

In the scanning electron microscope (SEM) or electron probe microanalyser (EPMA), the incident electron beam energy is typically below 40 keV and the image is formed by secondary or backscattered electrons that emerge from the surface of the specimen that is exposed to the incident electron beam. In such instruments it is desirable to measure thicknesses in certain types of specimens. A known method for measuring the thickness and composition of a thin layer on a substrate in the SEM or EPMA involves measuring the intensities of characteristic X-ray emissions for each chemical element. The specimen is struck by an electron beam with sufficient energy to penetrate through the layer to the substrate and the X-ray intensity for each element is divided by to the intensity produced when a pure bulk element standard is struck by the same beam, thereby obtaining a "k-ratio" for each element. The k ratios for a thin film will be less than unity. Suitable corrections to account for electron beam scattering by the layer and the substrate can be used to deduce the thickness and composition of the layer (e.g. J. L. Pouchou. "X-ray microanalysis of stratified specimens", Analytica Chimica Acta, 283 (1993), 81-97).

It has also been recognised that an unsupported layer or film can be analysed in the SEM or EPMA by the same approach used for analysing a layer on a substrate (Dijkstra et al, Microchimica Acta 114/115, 277-284, 1994). In this case, the unknown thin film is supported on the sort of grid typically used in the TEM so that at the highest available beam energy the incident beam will penetrate through the film and emerge into a vacuum rather than a substrate. The k-ratios for the characteristic element emissions are again measured by comparing the X-ray intensity relative to the intensity obtained when a bulk pure element is struck by the same incident beam. The thickness and composition of the film is deduced by modifying the applied corrections to take account of the lack of any scattering from the substrate. If the program cannot be modified so as to model the absence of a substrate, a suitable modification can be achieved by assuming that in place of a vacuum, there is a substrate of very low atomic number material, such as Beryllium, which would not produce significant back scattering.

As noted by Dijkstra et al, the same SEM or EPMA approach could in principle be used in the TEM. However, this is accompanied by a major disadvantage in that the X-ray yield from a bulk specimen increases strongly with incident electron energy. Therefore, when a pure bulk specimen is exposed to the same electron beam as is used to collect data from the thin specimen, the X-ray intensity, even at minimum beam current, causes an excessive count rate. Therefore, it is not practical to measure the X-ray intensities produced in the specimen and a pure bulk element standard using the same beam current. Boon (G. Boon, Thesis 2000 ISBN 90-386-2781-5) recognised this problem and devised a special beam current meter that could operate reliably over 3 to 4 decades. Boon recorded X ray data from the bulk standards at a much lower beam current than for the specimen to avoid overload of the X-ray spectrometer. The accurate beam current measurement enabled the correction of the X-ray intensities from specimen and the reference standard so that they corresponded to the same incident beam current and thus the k-ratios could be determined.

A further issue recognised by Dijkstra et al is that the penetration depth also increases strongly with incident electron energy, such that in the TEM, X-rays are generated at greater depths within the pure bulk element standard and are more likely to be absorbed as they emerge towards the detector. The required correction for absorption is therefore much higher at high electron energies and is particularly high for characteristic X-rays with low energy. In many TEMs, the X-ray detector is mounted so that it only detects X-rays emerging from the specimen surface at a shallow "take-off-angle". Such X-rays experience high absorption as they emerge from depth in the specimen. In order to reduce this absorption, the specimen surface can be tilted towards the X-ray detector, however this alters the penetration of incident electrons and complicates the correction calculations.

Whereas Boon had some success in applying X-ray corrections for a bulk pure sample with surface normal to the electron beam, he recognised that improvements were needed for analysis of light elements (low characteristic X-ray energy), and for tilted specimens. In addition, the need to measure beam currents and X-ray intensities from bulk standards for every element present renders the analysis of materials composed of several elements difficult.

There remains a strong need for a practical method of measuring the thickness of thin samples for use in electron microscopy.

SUMMARY OF THE INVENTION

In accordance with the invention we provide a method of measuring the mass thickness of a target sample for use in electron microscopy, comprising:

a. Obtaining reference data representative of the X-rays generated within a reference sample when a particle beam is caused to impinge upon a region of the reference sample, wherein in the region the reference sample has a predetermined thickness between its external surfaces of less than 300 nm and a predetermined mass thickness for at least one element;
b. Causing a particle beam to impinge upon a region of the target sample;
c. Monitoring the resulting X-rays generated within the target sample so as to produce monitored data; and,
d. Calculating output data including the mass thickness of the region of the target sample, based upon the monitored data and the reference data.

The method of the invention can be used to provide information on the mass thickness, that is, the product of density and linear thickness, and composition of a region of the target sample without requiring either measurements of the beam currents used, or measurements of X-ray spectra from bulk standards for each element being analysed. It will be understood that the term element is used here to mean a chemical element of the periodic table. By requiring only a single measurement of a thin (<300 nm) reference standard having known thickness and composition, the method allows the target sample to be analysed by simply replacing the reference standard under a particle beam with the unknown target sample rather than changing the beam current of the particle beam. Thus, the reference data is typically obtained by:

causing a particle beam to impinge upon the region of the reference sample; and, monitoring the resulting X-rays generated within the reference sample so as to produce the reference data.

The provision of a reference sample having known mass thickness and composition is important to the simplified analysis method of the invention. Preferably the region of the reference sample has a uniform thickness.

More preferably the region of the reference sample forms part of a continuous, unsupported thin film. That is to say, the region of the reference sample forms part of a film that is self-supporting in the sense that it is able to provide its own mechanical support and be cantilevered or suspended over a void, rather than being supported by a bulk substrate underneath. Thus, in the region, the reference sample may either comprise a thin film of reference material having known thickness and composition which is suspended over a void, that is with no supporting additional material underneath it or on its beam exit side, or it may comprise a layer of reference material deposited on a membrane or a series of layers of materials. In either case, the total thickness of all layers of reference sample material through which the particle beam passes and with which it interacts is thinner than a bulk substrate and is sufficiently thin in the direction of the beam that the intensity of the X-rays produced does not result in an excessive count rate. The total thickness of the reference sample in the region is defined by the distance between the two external surfaces. The external surfaces are the outside faces of the reference sample which form the outermost layers or portions on either side of the reference sample, at the interfaces between the sample and the void, vacuum, partial vacuum, gas or other environment in which it is situated. Since the method may preferably be carried out in a vacuum, the external surfaces form the faces of the sample at the vacuum-sample interfaces on opposite sides of the sample. Thus, when the reference sample comprises a thin film of known thickness and composition suspended over a void, its thickness is defined simply by the distance between the two outer faces of the film, and when the reference sample comprises a layer of reference material deposited on a membrane or multiple material layers, the reference sample thickness is defined by the distance between the outermost faces of the outermost layers of the whole assembly of layers. The thickness thus represents the distance between the point or plane at which the beam impinges upon the reference sample and the point or plane at which it emerges into the void or vacuum on the opposite side, having passed through any supporting layers.

The thicknesses of the specimen that are conventionally used in electron microscopy equipment such as transmission electron microscopes (TEM) typically vary across the specimens. These variations in the thickness of specimen material in the direction in which the electron beams are transmitted render such samples unsuitable for use in this method as the measured thickness will therefore depend upon the point on the sample at which the beam is positioned.

However, fabrication techniques exist that are able to produce foils or membranes having uniform thickness over an area sufficiently large to be easily identified upon the specimen whilst in the microscope. It is possible therefore to construct a suitable reference specimen using such a technique, and to be able to identify an area of known uniform thickness on the physical specimen so as to enable the positioning of an electron beam upon an area of known thickness using an electron microscope imaging facility. Preferably therefore, the region of the reference sample forms part of a larger portion of the reference sample, the larger portion having uniform thickness and composition.

Preferably, the uniform thickness of the larger portion of the reference sample is defined by the process by which it was manufactured. The availability of large batches of such reference membranes having been manufactured in large quantities and with a high degree of reproducibility and thickness uniformity is advantageous to the claimed method.

Although such manufacturing techniques make the provision of reference specimens having guaranteed predetermined thickness and composition possible, reference samples produced by these means may have the form of continuous, uniform thin films whose thicknesses and compositions are not precisely known. In order to predetermine these properties therefore, the reference specimen may be analysed by other methods. Typically, the thickness of the region of the reference sample may be predetermined using X-ray data obtained by way of a scanning electron microscope (SEM) or electron probe microanalyser (EPMA). Characterising the reference specimen by placing it in such equipment is possible using well known X-ray methods (for example Pouchou), wherein the intensities of characteristic X-rays generated within the film are compared with the intensity obtained from a bulk pure element standard in order to obtain a "k-ratio" for each elemental emission. The mass thickness and composition of the reference specimen may therefore be measured in this way.

Preferably, the thickness of the reference sample is of the same order of magnitude as the thickness of the target sample.

More preferably, the same X-ray detector is used to acquire each of the reference data and the target data, and the thickness of the reference sample is sufficiently similar to the thickness of the target sample that the intensity of X-rays generated within each of the target and reference samples is within the dynamic range of the X-ray detector. The selection of a reference specimen that has a thickness similar to that of the unknown target specimen allows the method to be carried out in absence of a beam current meter and corrections in order to account for changes in beam current. This is due to the two samples presenting similar thicknesses of material with which the particle beam interacts, and therefore producing similar quantities of X-ray radiation when exposed to the same incident electron beam. This similarity in X-ray yield may be achieved by selecting a reference sample whose thickness is within two, or more preferably one, order of magnitude of that for the target sample thickness. An X-ray detector that can function accurately over a wide range of input count rates will allow the invention to be used with a larger difference in thickness between reference and target samples. As detectors develop in future, for example, the target or reference could have a thickness from less than a nanometre up to 300 nm. The limit of 300 nm on thickness also ensures that X-ray production can be predicted more accurately without the complication of significant inelastic or sideways scattering of the incident electron beam.

The use of a single reference measurement upon a single reference specimen and no requirement for any further reference measurements is an important and advantageous aspect of the invention. Preferably, the acquisition of each of the reference and monitored data is performed using a detector having predetermined efficiency, and step d) is performed in accordance with the predetermined detector efficiency. Calibrating the X-ray detector used by the method so as to predetermine the X-ray detector efficiency characteristic is important in the calculation of mass thickness and composition performed at step d). If this property of the detector is well known, then a theoretical model may be used to predict the intensities for a characteristic X-ray emission from any element, in addition to simply those elements that are present in the reference specimen.

Typically the thickness of the region of the target sample is less than 300 nm.

Typically the particle beam at step a) has a first set of beam conditions and the particle beam at step b) has a second set of beam conditions. Preferably, the beam current of the first set of beam conditions is identical to the beam current of the second set of beam conditions. More preferably, the first set of beam conditions is identical to the second set of beam conditions. As previously mentioned, an advantage provided by the method over the invention is that any need to alter the beam current between measurements upon samples is avoided.

Although the use of a beam current meter is not required for the invention, a beam current measurement could be used for confirming the value of the beam currents incident upon the target and reference samples. If the current is different, the beam current could be adjusted to give the same beam current measurement value for both target and reference. Alternatively, any variation in the beam current of the first and second beam conditions could be mitigated by applying a correction to the calculation in accordance with these beam measurements. A relationship between the beam current of the first set of beam conditions and the beam current of the second set of beam conditions may be monitored, and the output data may be calculated in accordance with the monitored relationship between the beam currents. Moreover, each of the beam current of the first set of beam conditions and the beam current of the second set of beam conditions may be monitored, and the output data may be calculated in accordance with the monitored beam currents.

As previously explained, the calculated mass thickness is equal to the product of the density and the thickness of the region of the target sample in the direction of the particle beam.

Typically, the calculation at step b) includes calculating the absorption factor or one or more of the elements present in the target sample. The absorption experienced by generated X-rays within a sample, as mentioned previously, is incorporated into the calculation of the mass thickness and composition of the target sample in this way.

Typically the calculation at step d) includes generating simulated data representing X-rays generated within a simulated sample having a known relationship with the reference sample, calculating system conditions based upon the reference data and simulated data, and calculating output data including the mass thickness of the target sample, based upon the monitored data and the calculated system conditions.

The calculation at step d) may also include the estimation of the mass fraction of elements present in the target sample. Preferably therefore, in addition to the mass thickness of the region of the target sample, the output data further includes the mass fraction of one or more elements present in the target sample.

Typically, each length of time for which the X-rays are monitored is known, and step d) is performed in accordance with each known length of time.

Typically, the particle beam is an electron beam and preferably the energy of the electron beam is greater than 40 keV.

Typically, the region of the target sample may comprise a precipitate embedded in or supported on thin matrix material, and the output data at step (d) includes the mass thickness and composition of the precipitate. The method of the invention is particularly suited to transmission electron microscopes, wherein the high energy level of the electron beam (compared with equipment such as scanning electron microscopes), renders the use of bulk reference standards impractical. A TEM typically involves electron energies of the order of 200 keV. A bulk reference material placed under such a beam will produce an X-ray yield that is in excess of the dynamic range of the X-ray sensor that may be used to measure the target sample, and the sensor may be overloaded. Typically therefore the generating of X-rays and the recording of X-ray data are performed within a transmission electron microscope.

The calculation at step d) may be performed in a number of different ways. Preferably it is performed using an iterative computation that is performed until the difference between consecutive values of the mass thickness of the region of the target sample is less than a predetermined threshold. In this way, the iterative computation produces estimated values converging upon the mass thickness of the target sample. The computation may also produce estimated values converging upon the mass fraction of one or more of the elements present in the target sample.

BRIEF DESCRIPTION OF THE DRAWINGS

Some examples of methods and apparatus according to the invention are now described, with reference to the accompanying drawings, in which:—

DESCRIPTION OF EMBODIMENTS

Figure 1:
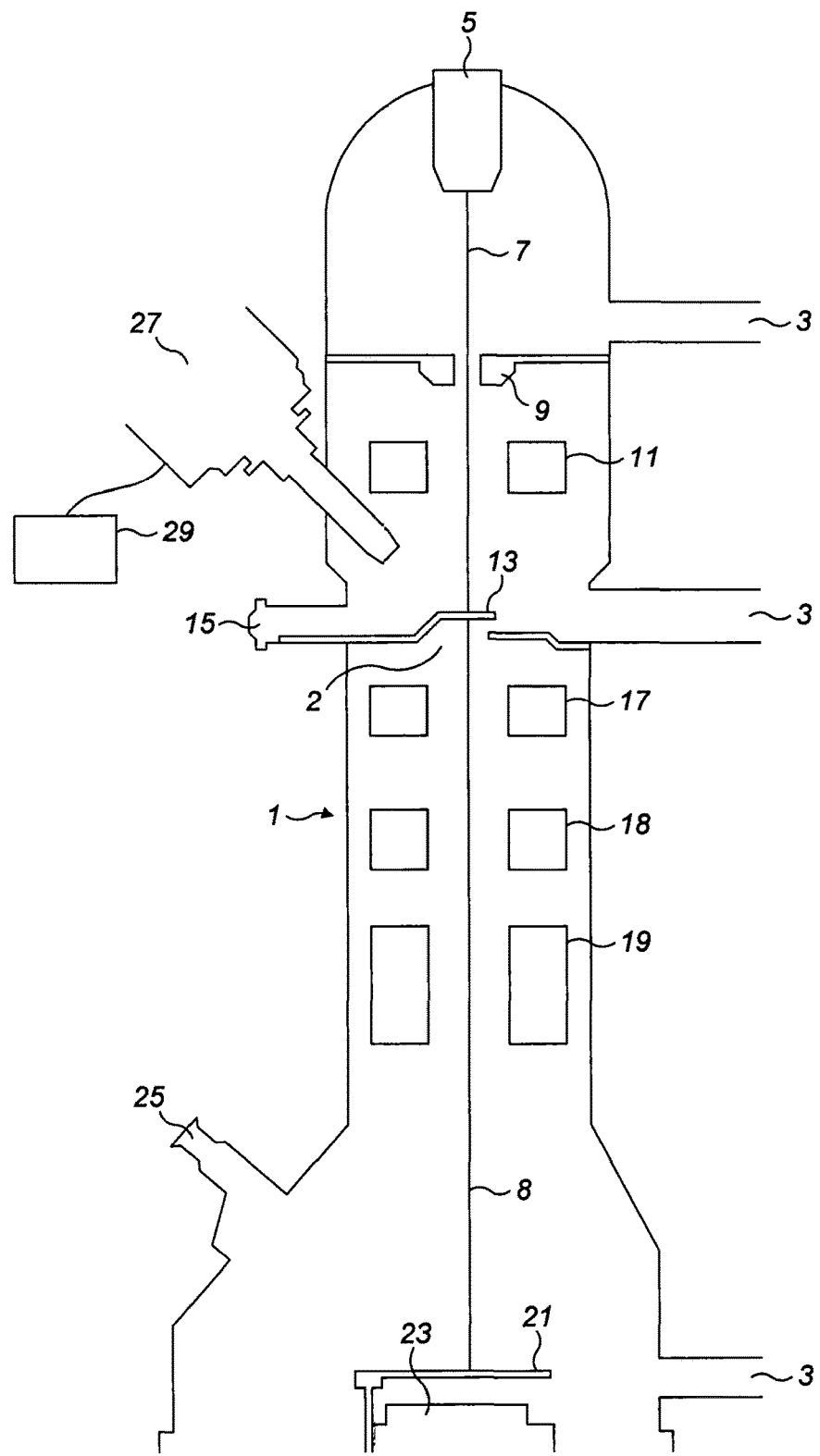
FIG. 1 is a schematic illustration of a transmission electron microscope apparatus for performing the claimed method.

We firstly describe apparatus suitable for the implementation of the method. A schematic diagram of the apparatus is shown in FIG. 1. This comprises a transmission electron microscope (TEM) 1. As is known in the art a TEM comprises a vacuum chamber 2 evacuated by way of pumping ports 3. The TEM further comprises an electron gun 5 for generating an electron beam 7. The electron beam is drawn from the electron gun along the TEM column by anode 9 and is focussed by condenser lens 11 onto a specimen held by a specimen grid 13. Access for inserting, removing and manipulating the specimen is provided by specimen port 15. Electrons 8 that are transmitted through a thin specimen (sufficiently thin to be partially electron transparent) continue to travel along the TEM column, being focussed by an objective lens 17, intermediate lens 18, and projector lens 19 so as to form an image on imaging plate 21 (essentially a screen). The image is recorded by an image recording device 23, and is observable through a window and/or via viewing binoculars 25, as is well known in the art. The TEM further comprises a side port through which X-ray detector 27 is directed at the specimen grid 13, the X-ray detector usually being located on the same side of the specimen as the incident electron beam 7. The X-ray detector is connected to a computer processor 29.

Figure 2:
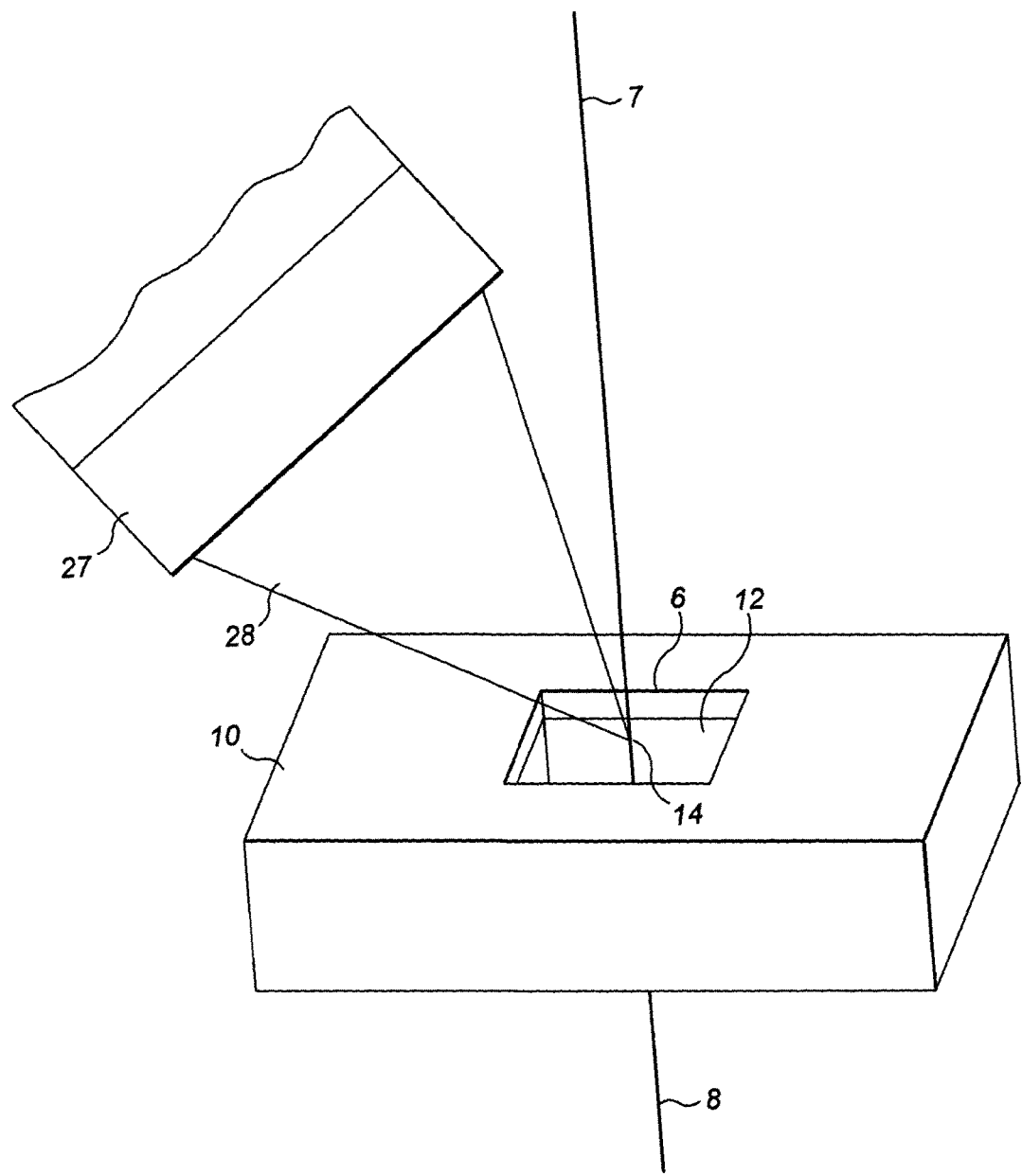
FIG. 2 shows an arrangement for the X-ray measurement of the reference sample in accordance with an example method.

With reference to FIG. 2 an example arrangement is shown of a reference sample 12 when located within the TEM 1 in accordance with the method to be described. A suitable "membrane" to use as the reference sample has a thickness of 50 nm, however other thicknesses, for example 30 nm, 100 nm or any thickness of a similar order would also be suitable. The reference sample 12 acts as a "standard" and should be selected such that the thickness of the reference sample 12 is of the same order of magnitude as the thickness of a target sample 16, the actual thickness of which is to be investigated by the method. The broad similarity in thicknesses between the reference sample 12 and target sample 16, ensures that the X-ray yields of both samples are within the dynamic range of the detector 27 when exposed to the same electron beam 7.

Suitable reference samples are available commercially in the form of silicon nitride membranes, which can be manufactured by semiconductor lithographic techniques. Previously, samples of this type have been used as alternative to typical TEM grids in supporting microscopy subjects such as cells and fibres. Such membranes typically achieve a high degree of uniformity in their thickness, and take the form of an unsupported silicon nitride membrane 12 across an aperture 6 within a silicon support frame 10. These frames may be made to fit standard TEM specimen holders, taking the place of the typically used grids.

In order to be able to locate upon the reference sample a suitable region that has predetermined thickness and composition, at which to direct the electron beam, the reference sample needs to have an area, within which the thickness and composition are known and uniform and which is identifiable when the sample is in the TEM.

In the current embodiment, the identifiable portion is formed by the 100 micron×100 micron square area within aperture 6, which is distinguishable within the TEM by virtue of it being the only transparent aperture within a surrounding support frame that is opaque to the incident beam. In the TEM, the distinctive transparent region would be visible while moving the reference sample around on the specimen stage.

In embodiments where a reference sample does not naturally feature a readily identifiable area of known thickness, it is possible to select and demarcate such a portion so that it may be located within the TEM. One example of an available alternative form of suitable reference sample comprises a grid containing an array of holes which are approximately one micron across or smaller. It is possible to deposit a thin film on such a grid such that the small region exposed by one or more of the holes has uniform thickness. Measuring the film thickness in SEM or microprobe for one or more holes over a small portion and depositing material, for example by electron beam induced deposition, on some of the surrounding holes, allows that known portion to be identified when the grid and film are inserted in the TEM or STEM instrument.

The uniformity of the thickness and composition of the identifiable portion should be within the degree of precision expected in the target thickness measurement. For example, should the required precision with which the target sample is to be measured be five percent, then the variation in the thickness and composition of the identifiable portion of the reference sample should not exceed five percent.

The manufacturing process for such reference samples is highly reproducible and consistent, therefore it is possible for the thickness and the composition of the reference sample 12 to be known (predetermined in a controlled manner) by virtue of being defined by the manufacturing process.

It is possible however, that a batch of membranes manufactured from a single semiconductor wafer will have similar, albeit unknown thicknesses and compositions. In this case, a sample from the batch may be placed on a sample holder in a scanning electron microscope (SEM) for analysis. For example, a 20 keV incident SEM electron beam may be directed upon the membrane and the intensity of silicon and nitrogen X-rays then measured and compared with the intensities of X-rays produced within bulk elemental standards using an identical beam current. Using these data, a thin film correction program iteratively calculates the mass thickness of the "film" (the reference sample 12) and the concentrations of silicon and nitrogen therein.

The thin film correction program does not measure each of the linear thickness t and the density $\rho$ individually, but does determine the product, which is the mass thickness $(\rho.t)$.

The product of the mass thickness and concentration C of a single element $(\rho.t).C$ is the mass thickness for that element.

If the sample is sufficiently thin and the energy of the X-ray line sufficiently high, then electron slowing-down and absorption will be negligible and the X-ray yield from a single element will be determined by the mass thickness for that element $(\rho.t).C$. The reference sample could therefore be a layer of material deposited on a membrane or a series of layers of materials. That is, the reference sample, the total thickness of which is sufficiently small to avoid the generation of excess X-rays when exposed to the electron beam, may comprise both the deposited layer and the membrane or series of layers. The thin film correction program could then regard the specimen as being constructed from a series of pure element layers and thus determine the effective mass thickness for a single element from the X-ray yield. Those skilled in the art would recognise that the mass thickness for a single element could thus be determined even if the total composition for all elements could not be determined and it would not matter if the reference sample had additional layers. In the case of a silicon nitride membrane, measurement of the low energy X-rays from nitrogen could be a problem but the higher energy silicon X-rays would suffer very little absorption. Therefore, it may be preferable to measure the mass thickness of silicon only, rather than attempt to measure the mass thickness and composition of the reference sample.

Figure 3:
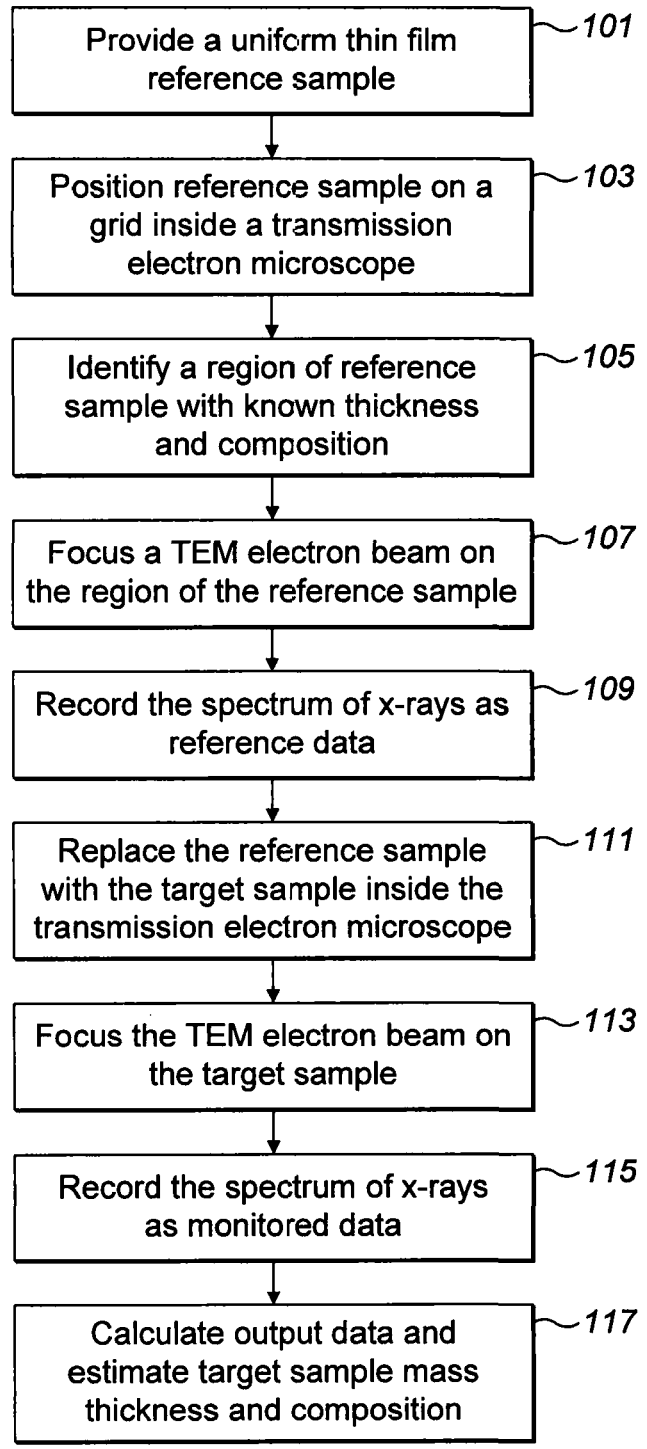
FIG. 3 is a flow diagram illustrating a first example method according to the invention.

Thus, a reference sample having a region of predetermined mass thickness and composition is provided for use in the example method now described below in association with FIG. 3.

The method begins at step 101 in which the reference sample 12 having the form of a thin film with uniform thickness, as described above, is provided.

At step 103 the reference sample is positioned under the beam within the transmission electron microscope 1.

At step 105 a region 14 having known, that is predetermined, thickness and composition is identified upon the reference sample. The reference sample has a large portion over which the thickness and composition are uniform, owing to the sample being prepared with a process that provides such physical and compositional homogeneity over extensive areas. Accordingly the desired region 14 is easy to locate under the beam 7 when the sample is positioned within the TEM Once the reference sample is mounted on the TEM grid, the electron microscope conditions, in particular the beam current, are adjusted to give a suitable X-ray count rate with a 200 keV incident electron beam. The TEM electron beam 7 is then focussed, at step 107, on the region 14 of the reference sample 12.

At step 109 the X-rays 28 that are produced by the interaction between the electrons and the region 14 of the reference sample are collected by detector 27. The detector collects an X-ray energy spectrum for a known acquisition period, and the intensities of characteristic X-ray emissions are obtained for each of the elements present in the reference sample. The intensity is embodied by the X-ray detection counts per second recorded for a spectral peak corresponding to a particular line series. The energy spectrum (in this case the intensity as a function of energy) of the X-rays is recorded as reference data.

At step 111 the reference sample is replaced by the target sample, that is, the specimen whose thickness is to be measured. The target sample is positioned upon a specimen grid 13 in a holder. A multi-specimen holder can accommodate both a specimen grid with the target sample and the reference sample so that both samples can be compared under identical conditions without turning off the beam. Alternatively, if the electron gun can be isolated from the main column, the target sample and reference sample may be exchanged using a "load lock" without altering the beam current.

The electron beam is then focussed upon the region 18 of the target sample 16 at step 113, with the beam current of electron beam 7 being identical to the current of the beam incident upon the reference sample 12 at step 107.

Figure 4:
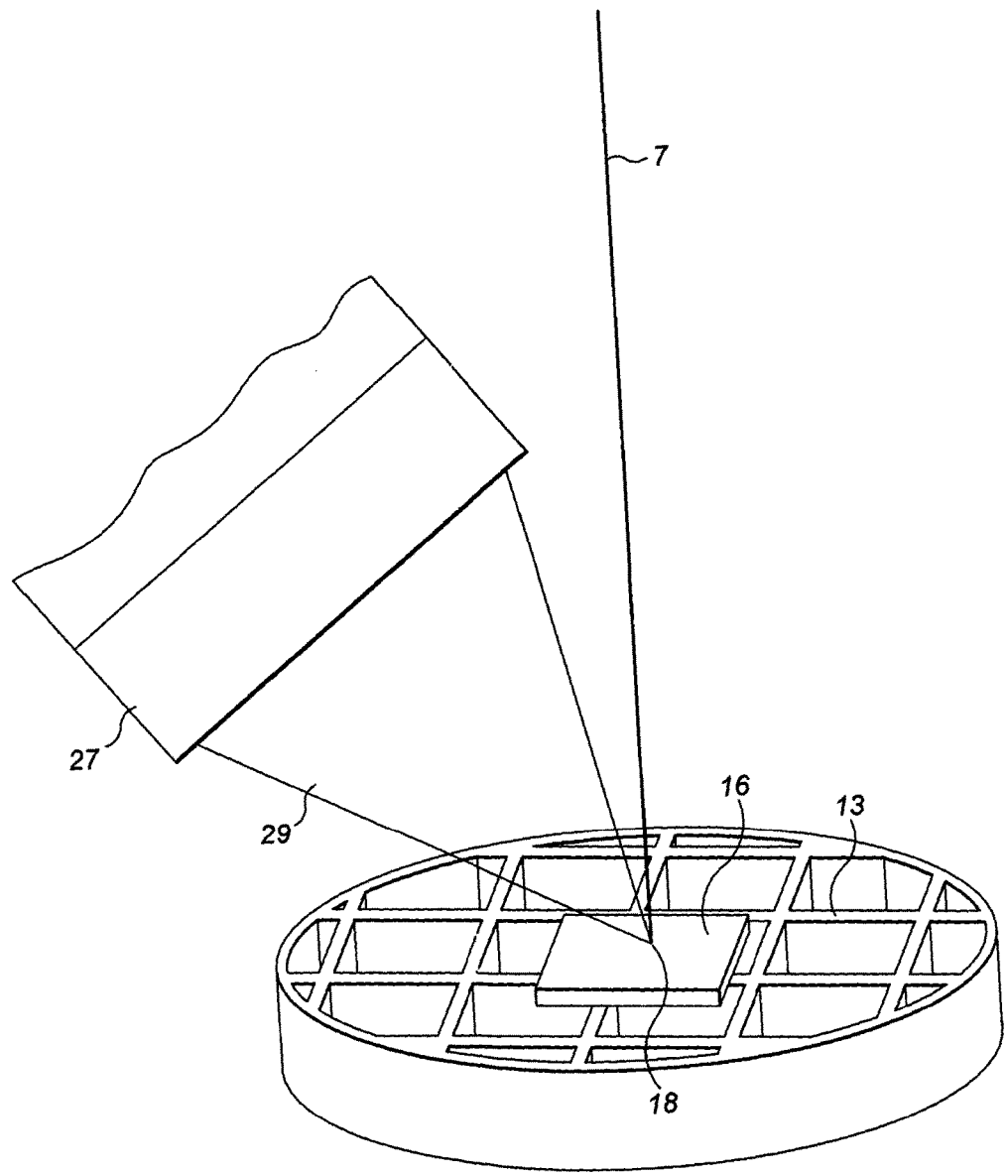
FIG. 4 shows the X-ray measurement of the target sample in an example method.

This is illustrated at FIG. 4. The spectrum of the X-rays 29 produced within the target sample is then recorded as monitored data at step 115 using a similar approach to that in step 109.

At step 117 the spectra recorded as reference and monitored data are then processed by computer processor 29 to calculate the output data and estimate the mass thickness and the composition of the target sample. The processing is performed by executing software embodying the computer implemented method now described.

For such a thin specimen having a thickness less than 300 nm, the 200 keV electron beam will not lose a significant fraction of its energy and will only suffer mild scattering effects, and therefore the X-ray ionisation cross-section will be virtually constant throughout the electron path. These considerations apply to measurements of both the reference and target samples and can be used to model the process. An example of how the recorded spectrum intensities P may be related to the mass thickness and composition of a sample is given by the equation:

$$P = (\rho \cdot t) \cdot C \cdot \left(\frac{N_0}{A}\right) Q \cdot f \cdot F(X) \cdot I \cdot \varepsilon \cdot \Omega/(4\pi) \quad (1)$$

Where $\rho$ is the density of the sample, t is the thickness of the sample and ($\rho$.t) is the mass thickness of the sample. C is the mass fraction for the element within the sample that gives rise to a particular peak P. For samples of uniform composition the mass fraction is the ratio of the mass of the element within the sample to the total mass of the sample. $N_0$ is Avogadro's number and A is the atomic weight of the element concerned. Q is the effective ionisation cross section. f is the fraction of ionisations which result in X-ray emission for the characteristic peak being measured. F(X) is the absorption factor for X-rays emerging from the sample in a direction towards the X-ray detector. I is the electron beam current, $\varepsilon$ is the detector efficiency and $\Omega$ is the collection solid angle for the X-ray detector 27.

The probability of an X-ray generated within a sample being absorbed depends upon the distance that it travels through the sample before emerging and therefore upon the point at which it is generated and its direction of travel. The absorption factor F(X) can be modelled for the case of ionisation being uniform throughout the specimen with equation:

$$F(X) = \frac{1 - \exp(-\mu(\rho \cdot t)\mathrm{cosec}(\theta))}{\mu \cdot (\rho \cdot t)\mathrm{cosec}(\theta)} \quad (2)$$

where $\mu$ is the mass absorption coefficient (cm$^2$/gm) for the characteristic X-rays in the specimen and $\theta$ is the X-ray take-off-angle. An average is taken for the mass absorption coefficients for all elements present in a sample, and $\mu$ is weighted in proportion to the mass fraction of each element.

Figure 5:
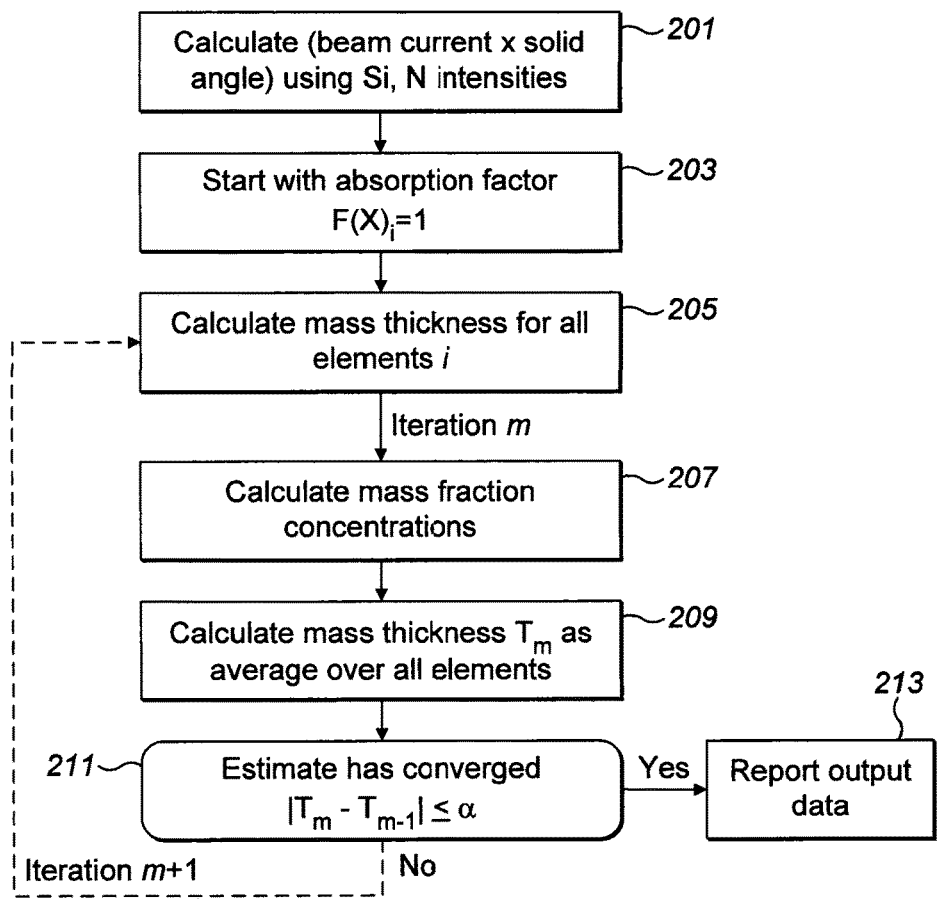
FIG. 5 is a flow diagram illustrating the thickness and composition calculation process of the example method; and, FIG. 6 is a flow diagram illustrating a second example method according to the invention.

An example method of calculating the output data as in step 117 is shown by the flow chart at FIG. 5.

At step 201 the effective product of electron beam current I and detector solid angle $\Omega$, more strictly $I\Omega(4\pi)$ from equation 1, is calculated. This is possible since the mass thickness and mass fraction of the reference sample, Avogadro's number and the atomic weight of the element are known. The efficiency of the detector may be determined for a range of energies, and the remaining factors may be calculated theoretically. By calculating the average of the results obtained by measurements on the silicon and nitrogen K line intensities from the reference sample membrane, the product of beam current and collection solid angle can be deduced. Alternatively, if the full composition of the reference sample is not known but the mass thickness of one element $(\rho.t).C$ is known, then the effective product of electron beam current I and detector solid angle can be determined from the predetermined mass thickness for a single element.

At step 203, the estimate of $I\Omega/(4\pi)$ from the reference measurement is used, along with a starting assumption that $F(X)_i=1$ for all elements i, representative of no absorption, to obtain a first estimate of the elemental mass thickness $(\rho.t).$ $C_i$ for each element i in the target sample. We denote this mass thickness parameter "$M_i$" for ease of reference.

If the target sample is inhomogeneous then the element mass thickness estimate $M_i$ can be useful to quantify the number of atoms per unit area being excited by the beam. If the sample is homogeneous then the ratio of the element mass thickness to the sum of the mass thicknesses for all of the elements in the sample gives an estimate of the mass fraction $C_i$. A first estimate of the target sample mass thickness $T_0$ (that is, a first estimate of $(\rho.t)$) can thus be obtained by averaging the results $M_i/C_i$ for all elements.

An iterative scheme is used in which the mass thickness and concentrations for the unknown specimen are adjusted such that the intensities predicted by equation 1 match those which are measurable. This is now described in more detail below. The number of iterative cycles are noted by using an incrementing index m, with the first cycle denote by m=1.

At step 205 the mass thickness $M_i$ is calculated for all elements i using the characteristic peak intensities $P_i$ for each element using equation 1.

At step 207 the mass fraction concentrations $C_i$ are calculated by taking the ratio between the mass thickness of an element to the total of all element mass thicknesses. This can be expressed as $C_i=M_i/\Sigma_i M_i$.

At step 209 a mass thickness estimate $T_m$ for the present iteration is then calculated as an average of $M_i/C_i$ for all elements.

The mass thickness estimate $T_m$ can be used to calculate the absorption factors for each element emission. Using increasingly accurate estimates of $F(X)_i$, the calculation process is repeated in order to obtain successively more accurate estimates of the mass thickness and mass fractions. The iteration cycles are continued until successive estimates are within a specified convergence criterion.

At step 211 the criterion condition: modulus $(T_m-T_{m-1})>\alpha$ is evaluated wherein $\alpha$ specifies a predetermined convergence limit. Thus, if the difference between successive mass thickness estimates is greater than this limit, then an improved absorption factor correction is computed for each element emission and the cycle continues. If successive mass thickness estimates are within the limit of $\alpha$, then at step 213 the final values for mass thickness $(\rho.t)$, that is $T_m$ and mass fractions $C_i$ of the elements present in the target sample are taken as the output data.

While such an example process may be used to calculate the output data, other iterative procedures and criteria for "goodness of fit" between predictions and measurements may equally be used.

One example where the sample is inhomogeneous is when a small precipitate is embedded in a matrix. It is possible to generalise the iterative method so as to determine the mass thicknesses and compositions of both the precipitate and the matrix. If the precipitate has mass thickness Mp and the matrix has mass thickness Mm in the direction of the beam and we have an estimate of the individual mass thicknesses of the elements Mi, then we can say that Mi=Mp*Cpi+ Mm*Cmi where Cpi and Cmi are the mass fractions of element i in precipitate and matrix respectively.

Thus, there are a series of N equations, one for each element present and there are a number of cases where these equations can be solved. Since the sum of mass concentrations for any material is 1, we have to determine (Np−1) mass concentrations and one mass thickness for the precipitate and (Nm−1) mass concentrations for the matrix and one mass thickness for the matrix. Thus, there are a total of (Np−1)+1+(Nm−1)+1=Np+Nm unknowns to be determined. If there are no elements common to both precipitate and matrix, then we immediately have Np+Nm equations available that can be solved for the unknowns. If there are one or more common elements, then the composition of the matrix can be determined by measurement of the matrix only in a region nearby to the precipitate to reduce the number of unknowns. If the precipitate is known by visual inspection to be on top of the matrix, then, with the same approximation of uniform ionisation throughout the specimen, the absorption for X-rays travelling towards the detector can be calculated in the same manner as for equation (2).

Thus, for some cases, the iterative method described for measuring the mass thickness and composition of a single film of material can be extended to determine the mass thickness and composition of a precipitate embedded or supported on thin matrix material.

A second example calculation method uses the equations for predicting the element intensity from a thin unsupported specimen relative to the intensity of a bulk pure element for the element for the beam energy being used. These "k-ratios" can be predicted for the elements in the membrane as the mass thickness and concentrations for the membrane are known. The intensity for a pure bulk element can therefore be derived from the measured intensity for each element in the reference membrane.

With a theoretical model of the intensity of pure bulk elements together with known values for the efficiency $\varepsilon$ of the X-ray detector at a range of energies, the intensity for any pure bulk element can be derived from the estimated intensity for a pure bulk element that is in the membrane. The measured intensity for each element in the target sample can be divided by the estimated intensity for a pure bulk element in order to obtain a k-ratio. The k-ratios for all elements can then be used to quantify the mass thickness and composition of the target sample, as described by Dijkstra et al.

Although this method also avoids the direct measurement of X-rays from bulk pure elements, the process requires a complex theoretical calculation that is critically dependent upon specimen geometry and may have limited accuracy particularly at low X-ray emission energies for which the effects of absorption within the samples are strong.

The above described example method therefore allows the mass thickness and composition of a thin film target sample to be measured within a transmission electron microscope without changing the beam current and without use of a bulk reference sample. However, it is possible to provide a variation of the above method in which the measurements of the spectra from the reference and target samples are taken using different beam currents respectively. If a beam current monitor is available, the beam currents which are caused to impinge upon each of the samples may be monitored and a suitable pro rata correction representative of the ratio between the beam currents may be applied if the current has changed between the two measurements. If a monitor is available that is not an accurate indicator of beam current but is highly reproducible (e.g. the signal from the TEM screen might serve as such an indicator), then if it is necessary to alter the beam between the measurements of the reference and target sample, then that monitor can be used to adjust the beam current so that it takes the same (unknown) value for both measurements. Ideally, a beam current monitor would not be necessary if the measurements could be completed quickly and the exposure of the target and reference samples to the same electron beam could be achieved with a simple specimen exchange mechanism which did not involve adjusting the beam. It should also be recognised that the order in which measurements of the target and reference sample are made is immaterial.

Figure 6:
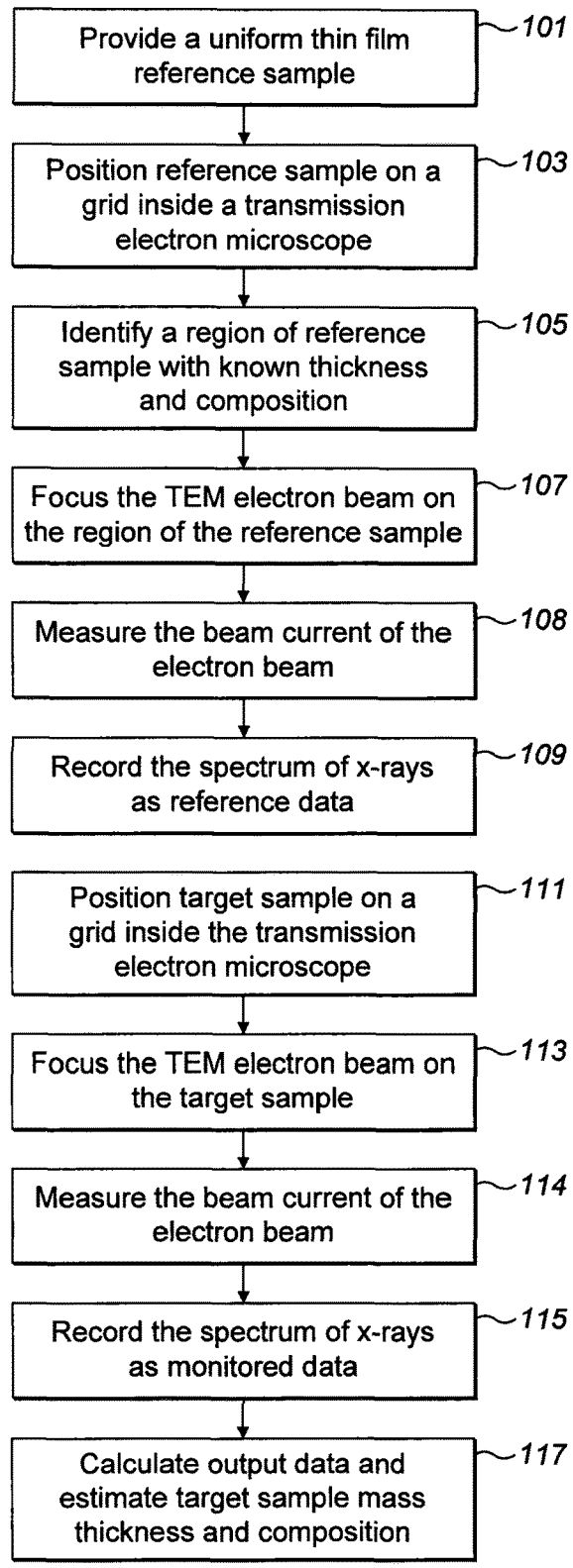

A second example of a method in accordance with the invention is illustrated by the flow chart at FIG. 6. The procedure shown is suitable for being carried out in microscopes wherein it is possible to measure the current of the electron beam.

The method is substantially the same as that described in relation to the first example, with the difference that it consists of an initial calibration step which is separated from the routine analysis. With reference to FIG. 6, this initial calibration process is illustrated by steps 101 to 109, wherein a spectrum of X-rays is calibration from the reference sample and is recorded as reference data, as previously described. This stage also includes the additional step 108 of measuring the beam current of the electron beam that is incident upon the reference sample. Performing this pre-calibration step allows the routine analysis steps 111 to 117, wherein a spectrum is recorded from an unknown target sample as reference data and the thickness and composition of the sample are calculated, without repeating the collection of an X-ray spectrum from the reference sample. This analysis stage includes the additional step 114 of measuring the beam current of the electron beam that is incident upon a target sample.

Monitoring the respective beam currents of the first and second sets of beam conditions at 108 and 114 allows the calculation at step 117 to be performed in accordance with the ratio between the measured beam currents in addition to the monitored and reference data. Thus, any target sample may be analysed using a beam current measurement instead of the measurement of the reference sample in the TEM with each execution of the method. Because this second method makes use of a thin reference sample, the beam current measurement only has to deliver proportionality over a much smaller range of currents than would be required for a bulk reference sample.

The invention claimed is:

1. A method of measuring the mass thickness of a target sample for use in electron microscopy, comprising:
   a. obtaining reference data from an electron beam instrument representative of the X-rays generated within a reference sample when an electron beam having a first set of beam conditions comprising a first beam current is caused to impinge upon a region of the reference sample, wherein in the region the reference sample has a predetermined thickness between its external surfaces of less than 300 nm and a predetermined mass thickness for a single element and wherein the region of the reference sample has a uniform thickness and forms part of a continuous, unsupported thin film;
   b. causing an electron beam having a second set of beam conditions comprising a second beam current, in the same electron beam instrument, to impinge upon a region of the target sample, wherein the first beam current is identical to the second beam current;
   c. monitoring the resulting X-rays generated within the target sample so as to produce monitored data; and
   d. calculating, independently of any beam current measurement, output data including the mass thickness of the region of the target sample, based upon the monitored data, the reference data, and the identical first and second beam currents.

2. A method according to claim 1 wherein at step (a) the reference data is obtained by:
   i. causing the electron beam to impinge upon the region of the reference sample; and
   ii. monitoring the resulting X-rays generated within the reference sample so as to produce the reference data.

3. A method according to claim 1 wherein the region of the reference sample forms part of a larger portion of the reference sample, the larger portion having uniform thickness and composition.

4. A method according to claim 3 wherein the variation in thickness of the reference sample within the portion is less than 5%.

5. A method according to claim 1 wherein the thickness of the region of the reference sample has been predetermined using X-ray data obtained by way of a scanning electron microscope or electron probe microanalysis.

6. A method according to claim 1 wherein the thickness of the reference sample is of the same order of magnitude as the thickness of the target sample.

7. A method according to claim 1, wherein the thickness of the reference sample is sufficiently similar to the thickness of the target sample such that the intensity of X-rays generated within each of the target and reference samples is within the dynamic range of the electron beam instrument.

8. A method according to claim 1 wherein the acquisition of each of the reference and monitored data is performed using the electron beam instrument having predetermined efficiency, and step (d) is performed in accordance with the predetermined efficiency.

9. A method according to claim 1 wherein the thickness of the region of the target sample is less than 300 nm.

10. A method according to claim 1 wherein the first set of beam conditions is identical to the second set of beam conditions.

11. A method according to claim 1 wherein the calculated mass thickness is equal to the product of the density and the thickness of the region of the target sample in the direction of the electron beam.

12. A method according to claim 1 wherein the calculation at step (d) includes calculating the absorption factor for one or more of the elements present in the target sample.

13. A method according to claim 1 wherein the calculation at step (d) includes generating simulated data representing X-rays generated within a simulated sample having a known relationship with the reference sample, calculating system conditions based upon the reference data and simulated data, and calculating output data including the mass thickness of the target sample, based upon the monitored data and the calculated system conditions.

14. A method according to claim 1 wherein the output data further includes the mass fraction of one or more of the elements present in the target sample.

15. A method according to claim 1 wherein each length of time for which the X-rays are monitored is known, and step (d) is performed in accordance with each known length of time.

16. A method according to claim 1 wherein the electron beam is an electron beam with energy greater than 40 keV.

17. A method according to claim 1 wherein the region of the target sample comprises a precipitate embedded in or supported on thin matrix material, and the output data at step (d) includes the mass thickness and composition of the precipitate.

\* \* \* \* \*